US007277757B2

(12) United States Patent
Casavant et al.

(10) Patent No.: US 7,277,757 B2
(45) Date of Patent: Oct. 2, 2007

(54) RESPIRATORY NERVE STIMULATION

(75) Inventors: David A. Casavant, Reading, MA (US); William J. Havel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 661 days.

(21) Appl. No.: 10/284,899

(22) Filed: Oct. 31, 2002

(65) Prior Publication Data

US 2004/0088015 A1    May 6, 2004

(51) Int. Cl.
*A61N 1/00* (2006.01)
(52) U.S. Cl. ....................................................... 607/42
(58) Field of Classification Search ................ 607/42, 607/2, 9, 4–5, 118; 600/484, 515, 516
See application file for complete search history.

(56) References Cited

U.S. PATENT DOCUMENTS

| 4,541,417 | A | | 9/1985 | Krikorian | |
|---|---|---|---|---|---|
| 5,935,078 | A | * | 8/1999 | Feierbach | 600/509 |
| 6,134,470 | A | * | 10/2000 | Hartlaub | 607/14 |
| 6,213,960 | B1 | | 4/2001 | Sherman et al. | |
| 6,234,985 | B1 | | 5/2001 | Lurie et al. | |
| 6,330,477 | B1 | | 12/2001 | Casavant | |
| 6,415,183 | B1 | * | 7/2002 | Scheiner et al. | 607/42 |
| 6,459,933 | B1 | | 10/2002 | Lurie et al. | |
| 6,490,489 | B2 | * | 12/2002 | Bornzin et al. | 607/122 |
| 6,580,946 | B2 | * | 6/2003 | Struble | 607/23 |
| 6,775,572 | B2 | * | 8/2004 | Zhu et al. | 607/14 |
| 6,922,587 | B2 | * | 7/2005 | Weinberg | 607/9 |
| 2001/0001126 | A1 | * | 5/2001 | Cammilli et al. | 607/5 |

FOREIGN PATENT DOCUMENTS

EP    0 838 233 A1    4/1998

OTHER PUBLICATIONS

Aaronson, K.D. et al., "Development and Prospective Validatio of a Clinical Index to Predict Survival in Ambulatory Patients Referred for Cardiac Transplant Evaluation," *Circulation*, vol. 95, p. 2660-67 (1997).
Criley, J.M. et al., "Cough-Induced Cardiac Compression. Self Administered Form of Cardiopulmonary Resuscitation," *JAMA*, vol. 236, No. 11, p. 1246-50 (1976).
Daggett, W.M. et al., "Intracaval Electrophrenic Stimulation. II. Studies on Pulmonary Mechanics, Surface Tension, Urine Flow and Bilateral Phrenic Stimulation," *J Thorac Cardiovasc Surg*, vol. 60, p. 98-107 (1970).

(Continued)

*Primary Examiner*—Carl Layno
*Assistant Examiner*—Jessica L. Reidel
(74) *Attorney, Agent, or Firm*—Daniel G. Chapik

(57) ABSTRACT

The invention is directed to an implantable medical device that stimulates a nerve associated with respiration. The nerve may, for example be a phrenic nerve, and the stimulation may cause a diaphragm of the patient to contract. The implantable medical device receives a signal that indicates a need for increased cardiac output and stimulates the nerve in response to the signal. The implantable medical device may receive such a signal by, for example, detecting a ventricular tachyarrhythmia, sensing a pressure that indicates a need for increased cardiac output, or receiving a signal from a patient via a patient activator. Stimulation of the nerve may increase cardiac output of a beating or defibrillating heart.

7 Claims, 7 Drawing Sheets

OTHER PUBLICATIONS

Glenn, W.W.L. et al., "Electrical Stimulation of Excitable Tissue by Radio-Frequency Transmission," *Ann Surg*, vol. 160, p. 338-45 (1964).

Ishii, K. et al., "Effects of Bilateral Transvenous Diaphragm Pacing on Hemodynamic Function in Patients After Cardiac Operations," *J. Thorac Cardiovasc Surg*, vol. 100, p. 108-14 (1990).

Khan, A.A. et al., "Right Hemidiaphragmatic Twitching: A Complication of Bipolar Atrial Pacing," *PACE*, vol. 20, No. 6, p. 1732-3 (1997).

Marozen, I. et al., "Life-Threatening Arrhythmia Stopped by Cough," *Cor Vasa*, vol. 32, No. 5, p. 401-8 (1990).

Miller, B. et al., "Cough-Cardiopulmonary Resuscitation in the Cardiac Catheterization Laboratory: Hemodynamic During an Episode of Prolonged Hypotensive Ventricular Tachycardia," *Cathet Cardiovasc Diagn*, vol. 18, No. 3, p. 168-71 (1989).

Moreira, L.F. et al., "Dynamic Cardiomyoplasty as a Therapeutic Alternative: Current Status," *Heart Fail Rev*, vol. 6, No. 3, p. 201-12 (Sep. 2001).

Petelenz, T. et al., "Self-Administered Cough Cardiopulmonary Resuscitation (c-CPR) in Patients Threatened by MAS Events of Cardiovascular Origin," *Wiad Lek*, vol. 51, No. (7-8), p. 326-36 (1998).

Saba, S.E. et al., "Sustained Consciousness During Ventricular Fibrillation: Case Report of Cough Cardiopulmonary Resuscitation," *Cathet Cardiovasc Diagn*, vol. 37, No. 1, p. 47-8 (1996).

Sarnoff, S.J. et al., "Electrophrenic Respiration," *Am J Physiol*, vol. 155, p. 1-9 (1948).

Stirbys, P. et al., "A Method for Estimating Endocardial Electrode Stability," *PACE*, vol. 13, No. 2, p. 1860-63 (1990).

Timmis, G.C. et al., "The Effect of Electrode Position on Atrial Sensing for Physiologically Responsive Cardiac Pacemakers," *Am Heart J*, vol. 108, No. 4, pt. 1, p. 909-16 (1984).

Voss, B. et al., "Dynamic Cardiomyoplasty: Evaluation of an Alternative Procedure in the Treatment of Terminal Heart Failure," *Z Kardiol*, vol. 90, Suppl. 1, p. 22-7 (2001).

* cited by examiner

RESPIRATORY NERVE STIMULATION

TECHNICAL FIELD

The invention generally relates to implantable medical devices (IMDs), and more particularly to techniques employed by IMDs to stimulate a nerve associated with respiration.

BACKGROUND

Heart failure refers to the inability of the heart to keep up with the functional demands made upon it. Congestive heart failure refers to an inability of the heart to pump an adequate amount of blood to the body tissues. In other words, congestive heart failure is characterized by inadequate cardiac output.

Because the heart is unable to pump an adequate amount of blood, blood returning to the heart becomes congested in the venous and pulmonary system. A patient with congestive heart failure may be unable to pump enough blood forward to provide an adequate flow of blood to his kidneys, for example, causing him to retain excess water and salt. His heart may also be unable to handle the blood returning from his pulmonary system, resulting in a damming of the blood in the lungs and increasing his risk of developing pulmonary edema.

Symptoms experienced by a patient with congestive heart failure may include breathing difficulty caused by pulmonary edema, swelling, particularly of the lower extremities, fatigue, difficulty concentrating, dizziness, and fainting. During periods where a patient with congestive heart failure is experiencing severe symptoms, breathing difficulty may be such that the patient cannot lie down to sleep, and the patient may feel as though they are suffocating.

Patients with congestive heart failure may be treated with pharmacological therapies to increase cardiac output. Some patients with congestive heart failure benefit from an implanted pacemaker that increases cardiac output by increasing the heart rate, or synchronizing the contraction of the ventricles of such patients. When a patient experiences severe symptoms, the patient may be admitted to hospital or clinic, and receive supplemental pharmacological therapy to alleviate the symptoms. This situation may be very costly because of the hospital stay, nursing costs, patient transportation costs, and so forth.

Another malady that may affect the cardiac output of a patient's heart is a tachyarrhythmia, such as ventricular tachycardia or ventricular fibrillation. Ventricular fibrillation is particularly life threatening because activity within the ventricles of the heart becomes so uncoordinated that virtually no pumping of blood takes place. With a brain deprived of oxygenated blood, the patient loses consciousness within a matter of seconds, and will die within minutes if not treated.

An electrical shock delivered to a fibrillating heart may repolarize the heart and cause it to reestablish a normal sinus rhythm. Patients who have experienced one or more episodes of ventricular fibrillation may receive an implanted pacemaker cardioverter-defibrillator (PCD). The PCD may detect the occurrence of ventricular fibrillation, charge an energy storage circuit, and deliver a defibrillation shock to the patient using the stored energy.

However, the charge time for a PCD typically ranges from seven to ten seconds when the PCD is new, but may be as long as twenty seconds as the energy storage circuit and power source age. Therefore, despite the implantation of a PCD, patients who have ventricular fibrillation episodes often collapse before a defibrillation shock is delivered. Because of the risk of collapse, some patients must modify their lifestyles by, for example, refraining from driving, riding a bicycle, swimming unattended, holding a grandchild, and the like. Further, falling from hemodynamic collapse frequently results in orthopedic injury, particularly in a patient of advanced age.

SUMMARY

In general, the invention is directed to techniques for stimulating a nerve associated with respiration of a patient. The nerve may be one or both of a right and a left phrenic nerve, and the stimulation may cause the diaphragm of the patient to contract. The implantable medical device may, for example, stimulate one or both of right and left phrenic nerves via intravascular leads that carry electrodes that are located in various positions within the heart or veins of the patient. Stimulation of such a nerve may cyclically decrease and increase the pressure within a thoracic cavity of the patient by changing the volume of the thoracic cavity. These pressure changes may increase cardiac output of a beating or defibrillating heart of the patient.

An implantable medical device for stimulating the nerve stimulates the nerve in response to a signal that indicates a need for increased cardiac output. The implantable medical device may receive such a signal by, for example, detecting a ventricular tachyarrhythmia, measuring the duration of intervals within cardiac cycles, sensing patient activity, sensing a pressure that indicates a need for increased cardiac output, sensing the oxygen saturation of the patients blood, or receiving a signal from a patient via a patient activator. The implantable medical device may be a pacemaker or a PCD, and may also pace the heart and/or provide defibrillation and cardioversion therapies to the patient. Where the implantable medical device paces the heart, the implantable medical device may stimulate the nerve by increasing the amplitude of at least some of the pacing pulses.

In one embodiment, the invention is directed to a method that includes receiving a signal that indicates a need for increased cardiac output of a heart of a patient, and stimulating a nerve associated with respiration of the patient in response to the signal. The nerve may be a phrenic nerve of the patient.

In another embodiment, the invention is directed to an implantable medical device that receives a signal that indicates a need for increased cardiac output of a heart of a patient, and stimulates a nerve associated with respiration of the patient in response to the signal. The implantable medical device may include a processor that receives a signal that indicates a need for increased cardiac output of a heart of a patient, and directs an output circuit to stimulate a nerve associated with respiration of the patient via the electrode in response to the signal. The nerve may be a phrenic nerve.

In another embodiment, the invention is directed to a computer-readable medium containing instructions. The instructions cause a programmable processor to receive a signal that indicates a need for increased cardiac output of a heart of a patient, and direct an output circuit to stimulate a nerve associated with respiration of the patient via an electrode in response to the signal.

In another embodiment, the invention is directed to a system that includes a monitor and an implantable medical device. The monitor senses physiological parameter of a patient that indicates a need for increased cardiac output via a sensor. The implantable medical device receives the sensed parameter and stimulates a nerve associated with respiration of the patient in response to the sensed parameter. The parameter may be a pressure or an oxygen saturation level.

The invention may be capable of providing a number of advantages. For example, the thoracic pressure changes caused by stimulation of a nerve associated with respiration, e.g., the phrenic nerve, may improve right atrial and ventricular filling, and increase stroke volume of the heart by decreasing relative afterload presented to the left ventricle during contraction. Over a number of cardiac cycles improved filling and stroke volume may lead to increased cardiac output of a beating heart, which may reduce the severity of symptoms associated with congestive heart failure. In some embodiments, a patient may conveniently request this therapy when experiencing symptoms via a patient activator.

Increased pressure within the thoracic cavity may cause oxygenated blood to flow from a fibrillating heart to the peripheral circulatory system of a patient in a similar manner to that caused by chest compressions provided during cardiopulmonary resuscitation (CPR). This blood flow may allow a patient who is experiencing ventricular fibrillation to maintain consciousness until appropriate defibrillation therapy, which may be provided by the implantable medical device, is delivered. Avoiding collapse in this manner may allow patients who have ventricular fibrillation episodes to experience an improved quality of life by allowing the patient to more safely engage in activities such as those listed above.

Further, because an implantable medical device according to the invention may take the form of a pacemaker or PCD using standard leads and lead configurations, a patient for whom pacing or antitachyarrhythmia therapy is indicated may receive these therapies in addition to respiratory nerve stimulation via a single implantable medical device. Providing multiple therapies via a single implantable medical device may advantageously reduce the amount of material implanted in the patient, reducing the likelihood of infection or other complications that are attendant to the implantation of medical devices within the human body.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
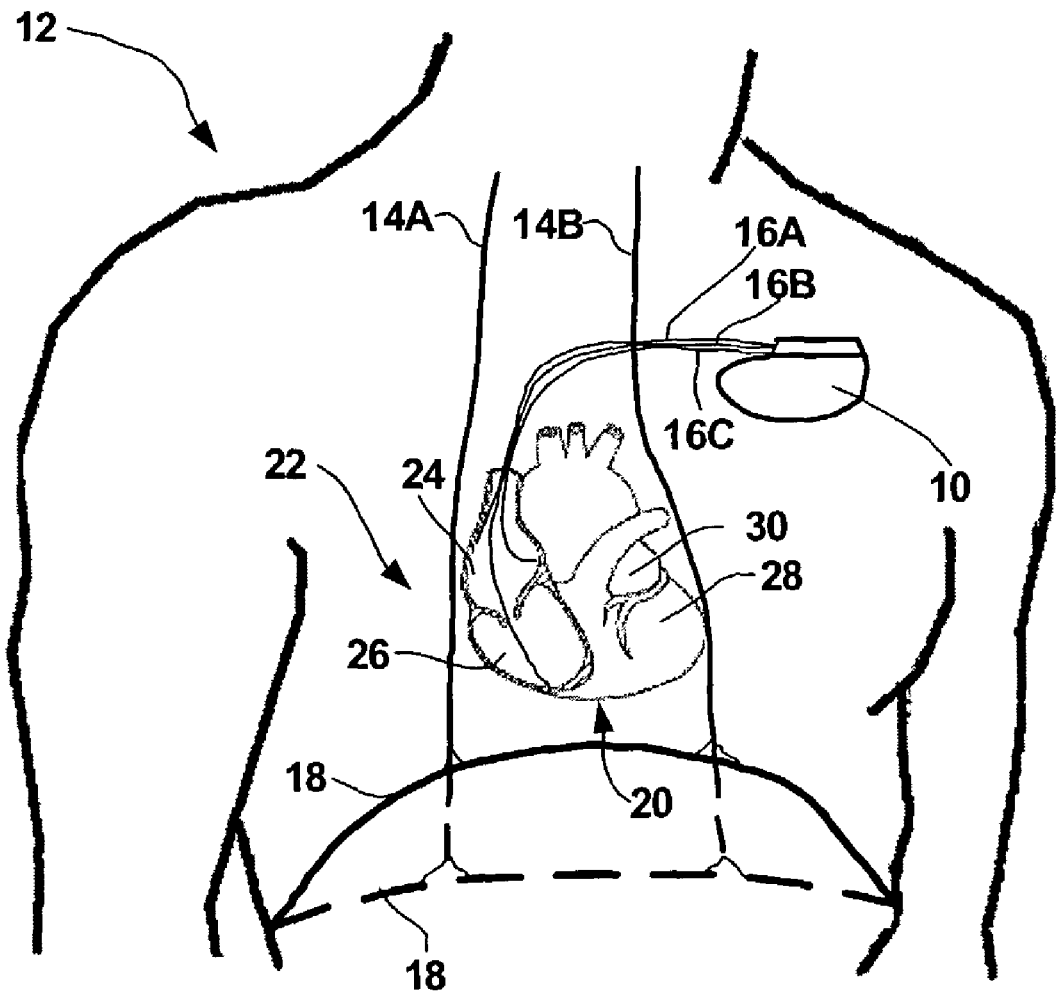
FIG. 1 is a schematic view of an implantable medical device.
Figure 1:
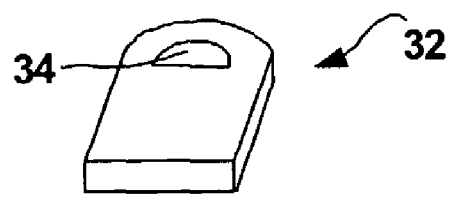

FIG. 1 is a schematic view of an implantable medical device ("IMD") 10 implanted within a patient 12. IMD 10 stimulates one or both of right phrenic nerve 14A and left phrenic nerve 14B (collectively "phrenic nerves 14") via one or more of leads 16A, 16B, and 16C (collectively "leads 16"), as shown in FIG. 1. Stimulation of phrenic nerves 14 by IMD 10 causes diaphragm 18 to contract. Repeated stimulation of phrenic nerves 14 by IMD 10 may, as will be described in greater detail below, increase the cardiac output of a beating or fibrillating heart 20. IMD 10 stimulates phrenic nerves 14 in response to a signal that indicates a need for increased cardiac output, as will be described in greater detail below.

IMD 10 may include any number of leads 16. Leads 16 may, as shown in FIG. 1, extend into heart 20. Leads 16 may be intravascular leads, i.e., enter heart 20 via one or more veins (not shown) of patient 12. The configuration of leads 16 shown in FIG. 1 is merely exemplary.

Each of leads 16 may include one or more electrodes (not shown) for delivering stimulation to phrenic nerves 14. These electrodes deliver stimulation to phrenic nerves 14 through the tissues of heart 20 or the veins. Leads 16 may also include electrodes by which IMD 10 may sense electrical activity within heart 20, e.g., sense electrical signals attendant to the depolarization and re-polarization of heart 20, deliver pacing pulses to heart 20, deliver defibrillation shocks to heart 20, and/or monitor pressure or oxygen saturation within heart 20 or otherwise within the cardiovascular system of patient 12. The electrodes for delivering stimulation to phrenic nerves 14, sensing electrical activity, and delivering pacing pulses may be unipolar or bipolar electrodes, as is well known in the art.

IMD 10 is not limited to use with intravascular leads 16, or intravascular or intracardiac electrodes. IMD 10 may deliver stimulation to phrenic nerves 14, sense electrical activity, deliver pacing pulses, deliver defibrillation shocks, and monitor pressure or oxygen saturation from any appropriate site within or outside of patient 12. For example, IMD 10 may stimulate phrenic nerves 14 via leads 16 that extend to any point along phrenic nerves 14, such as leads 16 that extend to a point of a phrenic nerve 14 near the neck of patient 12, and include coil electrodes that coil around phrenic nerves 14, as is known in the art.

When IMD 10 stimulates right phrenic nerve 14A, a right half of diaphragm 18 contracts. Similarly, when IMD 10 stimulates left phrenic nerve 14B, a left half of diaphragm 18 contracts. Depending on the strength of contraction of one of right and left halves of diaphragm 18, the other half of diaphragm 18 may be stimulated to contract via mechanical activation. Diaphragm 18 and phrenic nerves 14 are shown in FIG. 1 in their respective positions after diaphragm 18 has contracted as segmented lines. As shown in FIG. 1, when diaphragm 18 contracts, it descends, expanding the volume of thoracic cavity 22.

When diaphragm 18 is in the resting position, the pressure within thoracic cavity 22 is at an equilibrium pressure. When IMD 10 stimulates one or both phrenic nerves 14, causing diaphragm 18 to contract and thoracic cavity 22 to expand, the pressure within thoracic cavity 22 decreases relative to the pressure of the atmosphere outside of patient 12, causing air to enter the lungs (not shown) of patient 12. As air fills the lungs, the pressure within thoracic cavity 22 begins to return to the equilibrium pressure. When diaphragm 18 recoils, the pressure within thoracic cavity 22 increases beyond the equilibrium pressure, forcing air out of the lungs, until the equilibrium pressure is again reached.

When thoracic cavity 22 expands and the pressure within thoracic cavity 22 decreases, the pressure of blood within heart 20 and vessels (not shown) within thoracic cavity 22 may decrease relative to the pressure of blood within the extrathoracic vessels (not shown) of patient 10. When diaphragm 18 recoils and the pressure within thoracic cavity 22 increases beyond the equilibrium pressure, the pressure within heart 18 and the vessels within thoracic cavity 22 may increase relative to the pressure of blood within the extrathoracic vessels. The cyclical changes in the pressure of blood within heart 20 and the intrathoracic vessels relative to the extrathoracic vessels caused by repeated stimulation of phrenic nerves 14 by IMD 10 may lead to increased cardiac output of beating or defibrillating heart 20.

For example, during a period of right atrial and ventricular filling within a cardiac cycle of beating heart 20, a decrease in the pressure of blood within heart 20 and the intrathoracic vessels relative to the extrathoracic vessels may improve the filling of right atrium 24 and right ventricle 26, which receive blood from the extrathoracic vessels. Further, during contraction of left ventricle 28, an increase in the pressure of blood within heart 20 and the intrathoracic vessels relative to the extrathoracic vessels may decrease the relative afterload presented to the left ventricle 28 by the extrathoracic vessels, e.g., the pressure opposing the left ventricle as it contracts, increasing the stroke volume of left ventricle 28 for that contraction. Increased filling and stroke volume over a number of cardiac cycles will lead to increased cardiac output of a beating heart 20. Increased cardiac output of a beating heart 20 may, for example, reduce the severity of symptoms associated with congestive heart failure.

IMD 10 may stimulate phrenic nerves 14 at any time during a cardiac cycle. Further, IMD 10 need not stimulate phrenic nerves 14 during each cardiac cycle. IMD 10 may, for example, stimulate phrenic nerves 14 every other cycle or every third cycle in order to facilitate a more normal respiration pattern of patient 12.

Where IMD 10 delivers pacing pulses to right atrium 24, right ventricle 26, or left ventricle 28, IMD 10 may stimulate phrenic nerves 14 by increasing the amplitude of the pacing pulses in order to capture both heart 20 and one or both of phrenic nerves 14, depending on which chamber is receiving the pacing pulse. Thus, IMD 10 may stimulate phrenic nerves 14 at substantially the same time as a paced depolarization of atriums 24,30 or ventricles 26,28.

Where IMD 10 is not pacing heart 20, IMD 10 may stimulate phrenic nerves at substantially the same time as intrinsic events, such as depolarizations of atriums 24,30 or ventricles 26,28, by estimating when the intrinsic event will occur in any number of ways known in the art, and stimulating phrenic nerves 14 at the estimated time. For example, IMD 10 may sense these intrinsic events in order to estimate the heart rate, and deliver stimulation at substantially the same time as an intrinsic event based on the previous occurrence of that event and the heart rate. Where IMD 10 stimulates a phrenic nerve 14 via an electrode within one of chambers 24-28 of heart 20, it may be desirable to stimulate the phrenic nerve 14 at substantially the same time as a depolarization of that chamber so as to avoid causing a premature atrial or ventricular contraction by capturing the chamber with the stimulation. IMD 10 may also avoid causing a premature atrial or ventricular contraction by stimulating the phrenic nerve during the refractory period of that chamber.

Although IMD 10 may, consistent with the invention, stimulate phrenic nerves 14 at any time during a cardiac cycle of beating heart 20, it may be desirable to time the delivery of stimulation by IMD 10 within a cardiac cycle of heart 20 such that decreased pressure within thoracic cavity 22 occurs during filling of right atrium 24 and right ventricle 26, and increased pressure within thoracic cavity 22 occurs during contraction of left ventricle 28. The time for stimulation of phrenic nerves 14 that yields the best results may vary from patient to patient, and depend on heart rate, intensity of the stimulation and subsequent contraction of diaphragm 18, or like. Thus, IMD 10 may, in some cases, not deliver stimulation simultaneous with an intrinsic cardiac event, but may instead deliver stimulation at some time period after an intrinsic cardiac event is sensed.

During fibrillation of ventricles 26 and 28, cyclical changes in the pressure of blood within heart 20 and the intrathoracic vessels relative to the extrathoracic vessels caused by repeated stimulation of phrenic nerves 14 by IMD 10 may cause some circulation of blood through heart 20 and to the peripheral circulatory system (not shown) of patient 12. In particular, increased pressure within thoracic cavity 22 may cause oxygenated blood to flow from heart 20 to the peripheral circulatory system in a similar manner to that caused by chest compressions provided during cardiopulmonary resuscitation (CPR). The circulation caused by these cyclical pressure changes may allow patient 12 who is experiencing fibrillation of heart 20 to maintain consciousness until appropriate defibrillation therapy, which may be provided by IMD 10, is delivered. During ventricular fibrillation, IMD 10 may stimulate phrenic nerves 14 at any time, as fibrillating heart 20 has no organized cardiac cycle.

As mentioned above, IMD 10 stimulates phrenic nerves 14 in response to a signal that indicates a need for increased cardiac output. For example, IMD 10 may detect a tachyarrhythmia of ventricles 26 and 28, such as a ventricular fibrillation or tachycardia, as will be described in greater detail below. While ventricular fibrillation compromises cardiac output in an obvious way, ventricular tachycardia may also reduce cardiac output of heart 20 by reducing ventricular filling. IMD 10 may stimulate phrenic nerves 14 in response to the detection of either of these types tachyarrhythmias.

In some embodiments, IMD 10 may measure the duration of intervals within cardiac cycles or sense patient activity. IMD 10 may, for example, measure QT intervals within an electrogram of patient 12 sensed via one or more of the electrodes of leads 16, or receive signals indicating patient activity from an accelerometer (not shown). Shortened QT intervals or decreased patient activity may indicate a need for increased cardiac output.

In some embodiments, IMD 10 may cooperate with or include a monitor (not shown) that monitors a physiological parameter of a patient that indicates a need for increased cardiac output. The monitor may be a pressure monitor or an oxygen saturation monitor, both of which will be described in greater detail below. A pressure monitor may, for example, monitor the pressure within right ventricle 26 to estimate the pulmonary artery diastolic pressure based on the rate of change of the right ventricular pressure over time. Increased pulmonary artery diastolic pressure indicates inadequate cardiac output. A pressure monitor may also monitor arterial pulse pressure, central venous pressure, right ventricular end diastolic pressure, left ventricular end diastolic pressure, pulmonary capillary wedge pressure, or the like. An oxygen saturation monitor may monitor the oxygen saturation of hemoglobin within the arterial and/or venous blood of patient 10. Decreased arterial or venous oxygen saturation, or an increased difference between the arterial and venous oxygen saturations indicates inadequate cardiac output.

In some embodiments, IMD 10 may receive a signal from patient 12 indicating a need for increased cardiac output via patient activator 32. When patient 12 experiences symptoms of decreased cardiac output, such as difficulty breathing, patient 12 may place activator 32 over IMD 10, e.g., by placing activator 32 on the chest of patient 12, and press button 34 to request stimulation of phrenic nerves 14 by IMD 10. Activator 32 may deliver a signal indicating that patient 12 has pushed button 34 to IMD 10 via a telemetry circuit (not shown) of IMD 10. IMD 10 may stimulate phrenic nerves 14 in response to this signal. IMD 10 may, for example, stimulate phrenic nerves 14 for a predetermined period of time, until patient 12 again pushes button 34, or, if activator 32 delivers a continuous or periodic signal in response to the button push, until removal of activator 32 from the chest.

Figure 2:
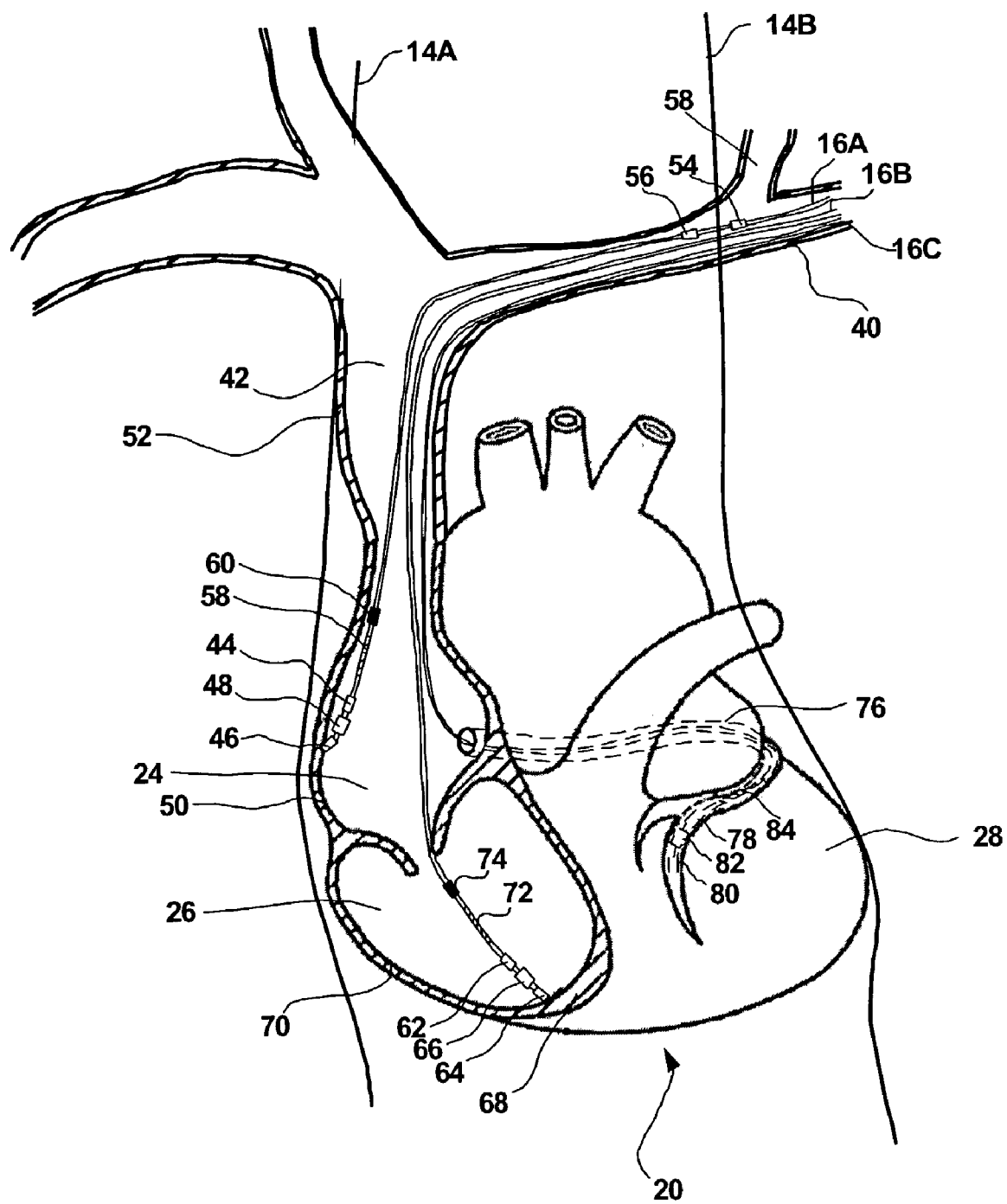
FIG. 2 is a schematic view illustrating the leads of the implantable medical device of FIG. 1.

FIG. 2 is a schematic view further illustrating leads 16 of IMD 10. Leads 16 may, as shown in FIG. 2, extend from IMD 10 and enter a left subclavian vein 40 of patient 12. As shown in FIG. 2, leads 16 may extend through left subclavian vein 40 and superior vena cava 42, and enter heart 20.

As shown in FIG. 2, lead 16A extends into right atrium 24. Lead 16A may include an elongated insulative lead body carrying a number of concentric coiled conductors separated from one another by tubular insulative sheaths. Located adjacent distal end of lead 16A are bipolar electrodes 44 and 46. Electrode 44 may take the form of a ring electrode, and electrode 46 may take the form of an extendable helix electrode mounted retractably within an insulative electrode head 48. Each of the electrodes 44 and 46 is coupled to one of the coiled conductors within the lead body. IMD 10 may stimulate right phrenic nerve 14A via electrodes 44 and 46. IMD 10 may also use electrodes 44 and 46 for atrial pacing and for sensing atrial depolarizations. In some embodiments, IMD 10 may include a separate lead 16 with separate electrodes, or separate electrodes on lead 16A for atrial pacing and sensing.

Electrodes 44 and 46 may, as shown in FIG. 2, be located proximate to a lateral wall 50 of right atrium 24. IMD 10 may more easily stimulate right phrenic nerve 14A when electrodes 44 and 46 are proximate to lateral wall 50. The distal end of lead 16A and electrodes 44 and 46 may, in some embodiments, be located proximate to a lateral wall 52 of superior vena cava 42.

In some embodiments, lead 16A may also, as shown in FIG. 2, include bipolar electrodes 54 and 56 located near the junction of left subclavian vein 40 and a left innominate vein 58. IMD 10 may stimulate left phrenic nerve 14B via electrodes 54 and 56. In other embodiments, IMD 10 may stimulate both phrenic nerves 14 with a single stimulus via a first unipolar electrode (not shown) located at the distal end of lead 16A, and a second unipolar electrode (not shown) located near the junction of left subclavian vein 40 and left innominate vein 58. In still other embodiments, electrodes 54 and 56 may be located on lead 16B, or on a lead 16 other than leads 16A-C.

Lead 16A may also, as shown in FIG. 2, include an elongated coil electrode 58 and a pressure sensor 60. Defibrillation electrode 58 and pressure sensor 60 may, as shown in FIG. 2, be located within right atrium 24, or may be located anywhere along lead 16A. IMD 10 may deliver defibrillation therapy to heart 20 via defibrillation electrode 58, and may monitor pressure within right atrium 24 and/or superior vena cava 42 via pressure sensor 60. Defibrillation electrode 58 may be fabricated from platinum, platinum alloy or other materials known to be usable in implantable defibrillation electrodes, and may be about 5 cm in length. Pressure sensor 60 senses the absolute pressure of blood within right atrium 24 and/or superior vena cava 42, and may be capacitive or piezoresistive pressure sensor. IMD 10 may, for example, monitor the central venous pressure of heart 20 via pressure sensor 60. Defibrillation electrode 58 and pressure sensor 60 may also be located on one or more leads other than lead 16A.

As shown in FIG. 2, lead 16B extends into right ventricle 26. Like lead 16A, lead 16B may include an elongated insulative lead body carrying a number of concentric coiled conductors separated from one another by tubular insulative sheaths. Located adjacent distal end of lead 16B are bipolar electrodes 62 and 64. Electrode 62 may take the form of a ring electrode, and electrode 64 may take the form of an extendable helix electrode mounted retractably within an insulative electrode head 66. Each of the electrodes 62 and 64 is coupled to one of the coiled conductors within the lead body. IMD 10 may stimulate right phrenic nerve 14A via electrodes 62 and 64. IMD 10 may also use electrodes 62 and 64 for ventricular pacing and for sensing ventricular depolarizations. In some embodiments, IMD 10 may include a separate lead 16 with separate electrodes, or separate electrodes on lead 16B for ventricular pacing and sensing.

Electrodes 62 and 64 may, as shown in FIG. 2, be located proximate to an apex 68 of right ventricle 26. IMD 10 may more easily stimulate right phrenic nerve 14A when electrodes 44 and 46 are proximate to apex 68. The distal end of lead 16B and electrodes 62 and 64 may, in some embodiments, be located proximate to a lateral wall 70 of right ventricle 26.

Like lead 16A, lead 16B may include an elongated coil electrode 72 and a pressure sensor 74 located within right ventricle 26. IMD 10 may deliver defibrillation therapy to heart 20 via defibrillation electrode 72, and may monitor pressure within right ventricle 26 via pressure sensor 74. IMD 10 may, for example, estimate a pulmonary artery diastolic pressure via pressure sensor 74. Defibrillation electrode 72 and pressure sensor 74 may be located on one or more leads other than lead 16B.

Lead 16C extends into a coronary sinus 76 of heart 20 until a distal end of lead 16 is proximate to left ventricle 28. Like leads 16A-B, lead 16C may include an elongated insulative lead body carrying a number of concentric coiled conductors separated from one another by tubular insulative sheaths. Located adjacent distal end of lead 16C are bipolar electrodes 78 and 80 indicated by a broken outline. Electrode 78 may take the form of a ring electrode, and electrode 80 may take the form of an extendable helix electrode mounted retractably within an insulative electrode head 82. Each of the electrodes 78 and 80 is coupled to one of the coiled conductors within the lead body. IMD 10 may stimulate left phrenic nerve 14B via electrodes 78 and 80. IMD 10 may also use electrodes 78 and 80 for ventricular pacing and for sensing ventricular depolarizations. Lead 16C may include an elongated coil electrode 84 indicated by a broken outline for delivery of defibrillation therapy to heart 20

IMD 10 may stimulate one or both of phrenic nerves 14 via any one of or combination of the bipolar and unipolar electrodes and electrode locations described above. Moreover, IMD 10 need not deliver pacing pulses to any chamber 24-28 of heart 20, need not deliver defibrillation therapy to heart 20, and need not monitor pressure within heart 20. The electrodes, sensors, and electrode and sensor locations are merely provided as examples of electrodes, sensors, and electrode and sensor locations that may be used in various embodiments of IMD 10.

Figure 3:
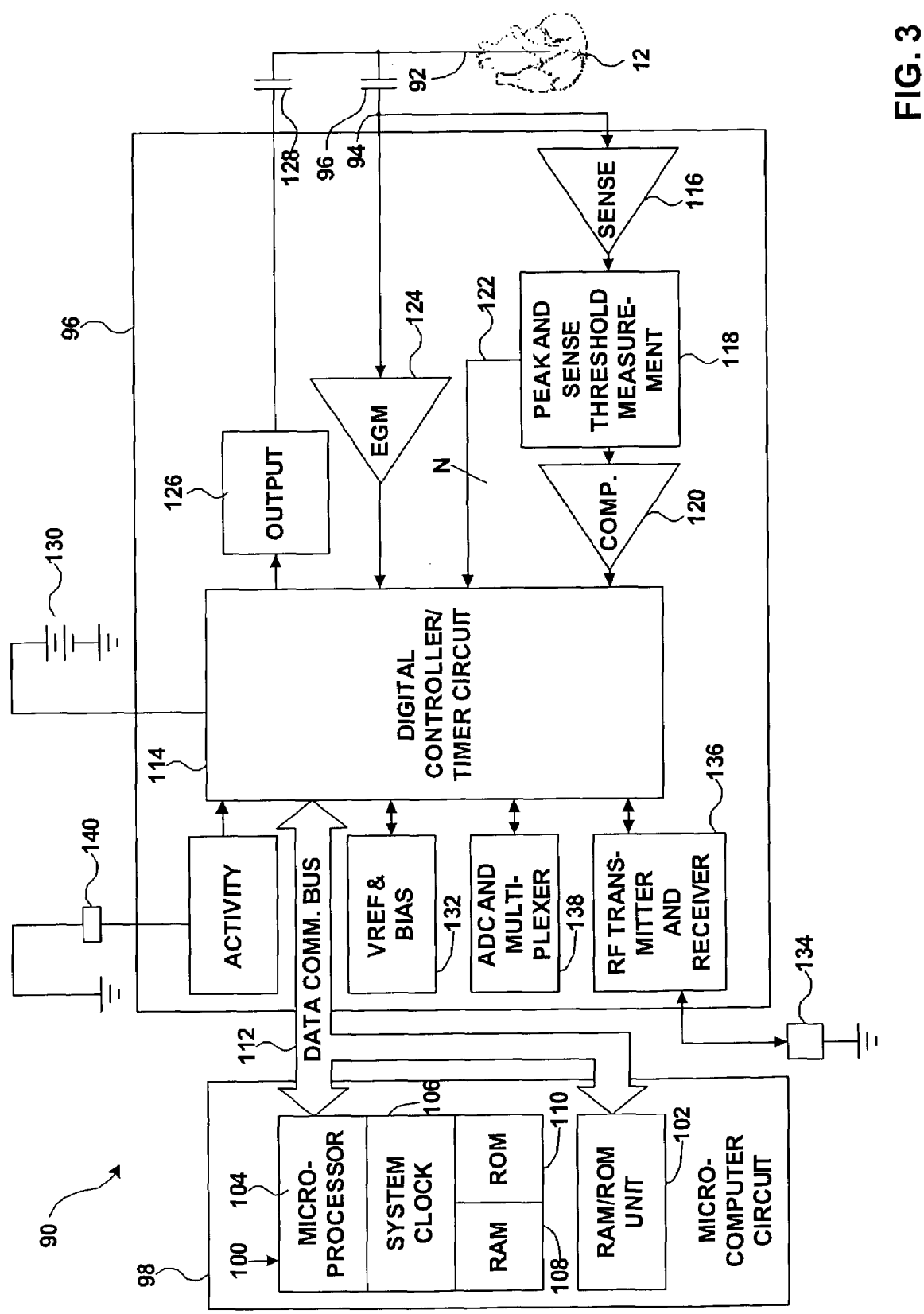
FIG. 3 is a block diagram illustrating constituent components of an implantable medical device.

FIG. 3 is a block diagram illustrating constituent components of an IMD 90 in accordance with one embodiment of the present invention. IMD 90 may be a pacemaker having a microprocessor-based architecture. For the sake of convenience, IMD 90 in FIG. 3 is shown with only a single lead 92 only connected thereto. IMD 90 may include any number of leads 92 to which similar circuitry and connections not explicitly shown in FIG. 3 may apply. Leads 92 may correspond to leads 16 of FIGS. 1 and 2.

As shown in FIG. 3, lead 92 is coupled to node 94 in IMD 90 through input capacitor 96. Input/output circuit 96 contains analog circuits for interfacing to lead 92 and circuits for the application of stimulation to one or both of phrenic nerves 14 and, in some embodiments, heart 20. The delivery of stimulation to phrenic nerves 14 may be controlled by software-implemented algorithms stored within microcomputer circuit 98. In embodiments where IMD 90 is also used to pace heart 20, software-implemented algorithms stored within microcomputer circuit 98 may also control the rate of heart 20.

Microcomputer circuit 98 preferably comprises on-board circuit 100 and off-board circuit 102. On-board circuit 100 preferably includes microprocessor 104, system clock circuit 106 and on-board RAM 108 and ROM 110. Off-board circuit 102 preferably comprises a RAM/ROM unit. On-board circuit 100 and off-board circuit 102 are each coupled by data communication bus 112 to digital controller/timer circuit 114. Microcomputer circuit 98 may comprise a custom integrated circuit device augmented by standard RAM/ROM components.

Operating commands for controlling the delivery of stimulation by IMD 90 are coupled by data bus 112 to digital controller/timer circuit 114. For example, software-implemented algorithms stored within microcomputer circuit 98 may cause processor 104 to direct digital controller/timer circuit 114 via data bus 112 to cause the stimulation of phrenic nerves 14 in response to a signal indicting a need for increased cardiac output. Where IMD 90 is used to pace heart 20, digital timers and counters of digital controller/timer circuit 114 establish the overall escape interval of the IMD 90, as well as various refractory, blanking and other timing windows for controlling the operation of peripheral components disposed within input/output circuit 96.

Digital controller/timer circuit 114 may be coupled to sensing circuitry, including sense amplifier 116, peak sense and threshold measurement unit 118 and comparator/threshold detector 120. Circuit 114 may also be coupled to electrogram (EGM) amplifier 124 for receiving amplified and processed signals sensed by lead 92. The electrogram signal provided by EGM amplifier 124 is employed when IMD 90 is being interrogated by an external programmer to transmit a representation of a cardiac analog electrogram. The electrogram signal may also be converted to a digital signal by ADC and multiplexer circuit 138 and provided microcomputer circuit 98 for digital signal analysis by microprocessor 104, which may, for example, analyze the signal using known techniques to measure QT interval durations, and determine a need for increased cardiac output based on the QT interval durations. For example, microprocessor 104 may compare the measured QT intervals or the rate of change of the QT intervals to a threshold value stored in one of memories 102, 108, and 110.

Sense amplifier 116 amplifies sensed electrical cardiac signals and provides an amplified signal to peak sense and threshold measurement circuitry 118, which in turn provides an indication of peak sensed voltages and measured sense amplifier threshold voltages on multiple conductor signal path 122 to digital controller/timer circuit 114. An amplified sense amplifier signal is then provided to comparator/threshold detector 120. Sense amplifier 116, peak sense and threshold measurement unit 118 and comparator/threshold detector 120 may be used by circuit 114 to detect intrinsic events within heart 20, such as depolarizations or repolarizations of atria or ventricles.

Output pulse generator 126 provides stimulation to phrenic nerves 14 through coupling capacitor 128 in response to signals provided by digital controller/timer circuit 114. Signals provided by digital controller/timer circuit 114 may control the amplitude, and other characteristics of the phrenic stimulation. High amplitude pulses may be provided by output pulse generator 126 in order to ensure capture of phrenic nerves 14 and adequate contraction of diaphragm 18. Twenty Volt pulses may, for example, be used. In some embodiments, output pulse generator 126 may deliver high frequency, e.g., 25-50 Hz, pulses to phrenic nerves 14 in order to cause more powerful gradational contractions of diaphragm 18. It may, however, be desirable to restrict delivery of high frequency pulses to situations in which IMD 90 delivers stimulation via electrodes outside of heart 20 in order to avoid causing an arrhythmia.

Digital controller/timer circuit 114 may also control the timing of stimulation of phrenic nerves 14. Circuit 114 may cause output pulse generator to deliver stimulation based on detected intrinsic cardiac events, or may deliver stimulation simultaneously with pacing pulses, as described above with reference to FIG. 1. Where IMD 90 also paces heart 20 via output pulse generator 126, output pulse generator 126 may provide pacing stimuli to heart 20 through coupling capacitor 98 in response to a pacing trigger signal provided by digital controller/timer circuit 114 each time the escape interval times out, an externally transmitted pacing command is received or in response to other stored commands as is well known in the pacing art. Circuit 114 may direct output pulse generator 126 to increase the amplitude of pacing pulses in order to stimulate phrenic nerves 14, as described above. In some embodiments, IMD 90 may include separate leads 92, sensing circuitry 116-120, and output pulse generators 126 for pacing, and leads 92 and output pulse generators 126 for delivering stimulation to phrenic nerves 14.

Electrical components shown in FIG. 3 are powered by an appropriate implantable battery power source 130 in accordance with common practice in the art. For the sake of clarity, the coupling of battery power to the various components of IMD 90 is not shown in the FIG. 3. $V_{REF}$ and Bias circuit 132 most preferably generates stable voltage reference and bias currents for analog circuits included in input/output circuit 96.

Antenna 134 is connected to input/output circuit 96 to permit uplink/downlink telemetry through RF transmitter and receiver telemetry unit 136. Telemetry unit 136 may receive a signal indicating a need for increased cardiac output from patient activator 32 (FIG. 1) via antenna 134. Further, IMD 90 may be programmable by means of an external programming unit (not shown) via antenna 134 and telemetry unit 136. One such programmer is the commercially available Medtronic Model 9790 programmer, which is microprocessor-based and provides a series of encoded signals to IMD 90, typically through a programming head which transmits or telemeters radio-frequency (RF) encoded signals to IMD 90. Where IMD 90 is a rate responsive pacemaker for example, rate response parameters may be programmed using the programmer. Analog-to-digital converter (ADC) and multiplexer unit 138 digitizes analog signals and voltages to provide "realtime" telemetry intracardiac signals and battery end-of-life (EOL) replacement functions.

IMD 90 may include activity sensor or accelerometer 140. Activity sensor 140 typically (although not necessarily) provides a sensor output that varies as a function of a measured parameter relating to a patient's metabolic requirements. The output signal provided by activity sensor 140 is coupled to input/output circuit 96. Microprocessor 104 may receive the output signal provided by activity sensor 140, and determine whether increased cardiac output is required. Microprocessor 104 may compare the output signal to a threshold value stored in one of memories 102, 108 and 110.

Figure 4:
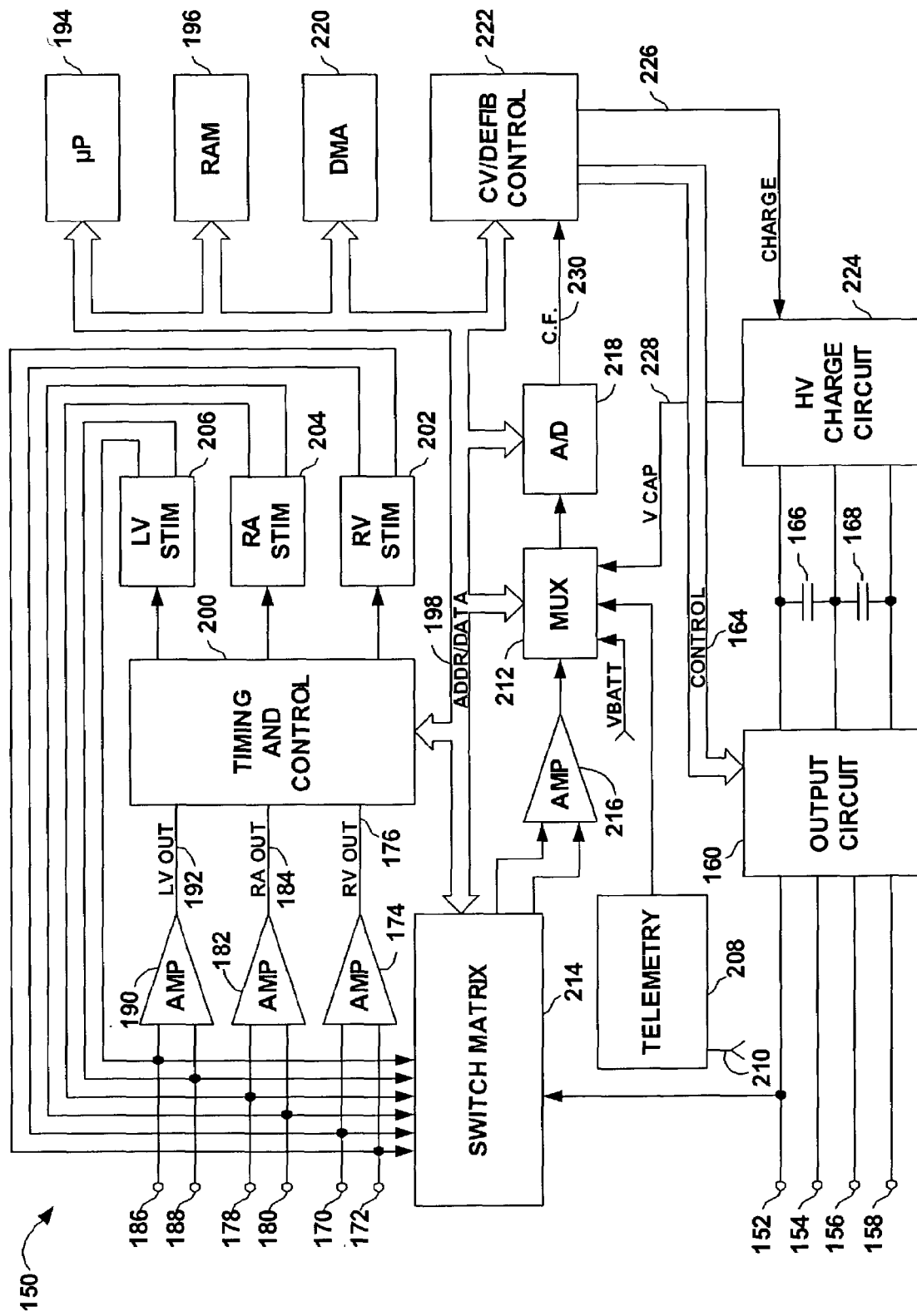
FIG. 4 is a block diagram illustrating constituent components of another implantable medical device.

FIG. 4 is a block diagram illustrating constituent components of another IMD 150. IMD 150 may be a pacemaker-cardioverter-defibrillator (PCD) having a microprocessor-based architecture. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies. Alternatively, IMD 150 may be an implantable nerve stimulator or muscle stimulator. The present invention is believed to find wide application to any form of implantable electrical device for use in conjunction with electrical leads.

IMD 150 is provided with an electrode system. Electrodes 152, 154, 156 and 158 are coupled to high voltage output circuit 160, which includes high voltage switches controlled by CV/defib control logic 162 via control bus 164. Switches disposed within circuit 160 determine which electrodes are employed and which electrodes are coupled to the positive and negative terminals of the capacitor bank (which includes capacitors 166 and 168) during delivery of defibrillation pulses. Electrodes 152-156 may correspond to defibrillation electrodes 58, 72 and 84 of FIG. 2. Electrode 158 in FIG. 4 may correspond to an uninsulated portion of the can of IMD 150.

Electrodes 170 and 172 are located on or in right ventricle 26, and are coupled to an R-wave amplifier 174, which preferably takes the form of an automatic gain controlled amplifier providing an adjustable sensing threshold as a function of the measured R-wave amplitude. Electrodes 170 and 172 may correspond to electrodes 62 and 64 of FIG. 2. IMD 150 may stimulate right phrenic nerve 14A, and may, in some embodiments, deliver pacing pulses to right ventricle 26 via electrodes 170 and 172. R-wave amplifier 174 may be used to detect intrinsic ventricular depolarizations. A signal is generated on RV-out line 176 whenever the signal sensed between electrodes 170 and 172 exceeds the present sensing threshold.

Electrodes 178 and 180 are located on or in right atrium 24, and are coupled to the P-wave amplifier 182, which preferably also takes the form of an automatic gain controlled amplifier providing an adjustable sensing threshold as a function of the measured P-wave amplitude. Electrodes 178 and 180 may correspond to electrodes 44 and 46 of FIG. 2. IMD 150 may stimulate right phrenic nerve 14A, and may, in some embodiments, deliver pacing pulses to right atrium 24 via electrodes 178 and 180. P-wave amplifier 182 may be used to detect intrinsic atrial depolarizations. A signal is generated on RA-out line 184 whenever the signal sensed between electrodes 178 and 180 exceeds the present sensing threshold.

Electrodes 186 and 188 are located in the coronary sinus 76 of heart 20 proximate to left ventricle 28, and are couples to R-wave amplifier 190, which preferable also takes the form of an automatic gain controlled amplifier providing an adjustable sensing threshold as a function of the measured R-wave amplitude. Electrodes 186 and 188 may correspond to electrodes 78 and 80 of FIG. 2. IMD 150 may stimulate left phrenic nerve 14B, and may, in some embodiments, deliver pacing pulses to left ventricle 28 via electrodes 186 and 188. R-wave amplifier 190 may be used to detect intrinsic ventricular depolarizations. A signal is generated on LV-out line 192 whenever the signal sensed between electrodes 186 and 188 exceeds the present sensing threshold.

In some embodiments, IMD 150 may include additional electrodes (not shown). For example, IMD 150 may include electrodes that correspond to electrodes 54 and 56 of FIG. 2. These electrodes may be located near the junction of left subclavian vein 40 and a left innominate vein 58, and IMD 150 may stimulate left phrenic nerve 14B via these electrodes.

The delivery of stimulation to phrenic nerves 14 may be controlled by microprocessor 194 according to software-implemented algorithms stored within a memory 196, such as a RAM. In embodiments where IMD 150 is also used to pace heart 20, software-implemented algorithms stored within memory 196 may also control the rate of heart 20. Operating commands for controlling the delivery of stimulation by IMD 150 are coupled by data bus 198 to timing and control circuit 200.

For example, the software-implemented algorithms executed by microprocessor 194 may cause microprocessor 194 to direct circuit 200 via data bus 198 to cause the stimulation of phrenic nerves 14 in response to a signal indicting a need for increased cardiac output. Circuit 200 may control the timing of stimulation of phrenic nerves 14, as discussed above. For example, circuit 200 may cause one or more of stimulation output circuits 202-206, which are coupled to electrodes 170, 172, 178, 180, 186 and 188, to deliver stimulation to one or both of phrenic nerves 14 based on detected intrinsic cardiac events, such as detected P-waves or R-waves, or simultaneous with pacing pulses, as described above with reference to FIG. 1.

IMD 150 may use stimulation circuit 202 and/or stimulation circuit 204 to stimulate right phrenic nerve 14A. IMD 150 may use stimulation circuit 206 to stimulate left phrenic nerve 14B. IMD 150 may also use additional stimulation circuits (not shown) to stimulate right or left phrenic nerves 14. For example, IMD 150 may use a stimulation circuit coupled to electrodes that correspond to electrodes 54 and 56 of FIG. 2, located near the junction of left subclavian vein 40 and a left innominate vein 58, in order to stimulate left phrenic nerve 14B.

Signals provided to stimulation circuits 202-206 by timing/control circuit 200 may control the amplitude, and other characteristics of the phrenic stimulation. High amplitude pulses may be provided by stimulation circuits 202-206 in order to ensure capture of phrenic nerves 14 and adequate contraction of diaphragm 18. Twenty Volt pulses may, for example, be used. Where IMD 150 paces heart 20 via one or more of stimulation circuits 202-206, circuit 200 may direct one or more stimulation circuits 202-206 to increase the amplitude of pacing pulses in order to stimulate phrenic nerves 14, as described above.

In some embodiments, stimulation circuits 202-206 may deliver high frequency, e.g., 25-50 Hz, pulses to phrenic nerves 14 in order to cause more powerful gradational contractions of diaphragm 18. It may, however, be desirable to restrict delivery of high frequency pulses to situations in which IMD 150 delivers stimulation via electrodes outside of heart 20 in order to avoid causing an arrhythmia. Where IMD 150 is used to detect and treat arrhythmias, and IMD 150 has detected a ventricular fibrillation, processor 194 may direct timing/control circuit 200 to direct one or more of stimulation circuits 202-206 to deliver high frequency pulses, because defibrillation therapy eventually delivered by IMD 150 will counteract the pro-arrhythmic effects of the high frequency stimulation on heart 20.

Where IMD 150 is used to pace heart 20, circuit 200 may include programmable digital counters which control the basic time intervals associated with DDD, VVI, DVI, VDD, AAI, DDI and other modes of single, dual and three chamber pacing well known to the art. For example, circuit 200 may control the time intervals associated with biventricular cardiac resynchronization therapy. Circuit 200 also preferably controls escape intervals associated with anti-tachyarrhythmia pacing in right atrium 24, right ventricle 26, and/or left ventricle 28, employing any anti-tachyarrhythmia pacing therapies known to the art.

Intervals defined by circuit 200 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 194, in response to stored data in memory 196 and are communicated to pacing circuitry 200 via address/data bus 198. Circuit 200 also determines the amplitude of the cardiac pacing pulses under control of microprocessor 194.

During pacing, escape interval counters within timing/control circuitry 200 are reset upon sensing of R-waves and P-waves as indicated by a signals on lines 176, 184 and/or 192, and in accordance with the selected mode of pacing on time-out trigger generation of pacing pulses by stimulation circuitry 202, 204, or 206. Escape interval counters are also reset on generation of pacing pulses and thereby control the basic timing of cardiac pacing functions, including anti-tachyarrhythmia pacing. The durations of the intervals defined by escape interval timers are determined by microprocessor 194 via address/data bus 198. Where IMD 150 is used to detect the presence of tachyarrhythmias, the value of the count present in the escape interval counters when reset by sensed R-waves and P-waves may be used to measure the durations of R-R intervals, P-P intervals, P-R intervals and R-P intervals may be stored in memory 196 and used by microprocessor 194 to detect the presence of tachyarrhythmias.

Microprocessor 194 most preferably operates as an interrupt-driven device, and is responsive to interrupts from timing/control circuit 200 corresponding to the occurrence of sensed P-waves and R-waves and corresponding to the generation of cardiac pacing pulses. Those interrupts are provided via address/data bus 198. Any necessary mathematical calculations to be performed by microprocessor 194 and any updating of the values or intervals controlled by timing/control circuit 200 take place following such interrupts.

Telemetry circuit 208 may receive a signal indicating a need for increased cardiac output from patient activator 32 (FIG. 1) via antenna 210. The signal may be provided to microprocessor 194 via multiplexer 212 and address/data bus 198. Further, IMD 150 may be programmable by means of an external programming unit (not shown) via antenna 210 and telemetry unit 208, as described above with reference to IMD 90 of FIG. 2.

As mentioned above, IMD 150 may also receive a signal indicating a need for increased cardiac output by detecting a tachyarrhythmia, such as a ventricular tachycardia or fibrillation. As mentioned above, microprocessor 194 may detect tachyarrhythmias based on durations of R-R intervals, P-P intervals, P-R intervals and R-P intervals stored in memory 196. Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time.

Microprocessor 194 may also detect tachyarrhythmias using digital signal processing techniques. Switch matrix 214 is used to select which of the available electrodes are coupled to wide band (0.5-200 Hz) amplifier 216 for use in digital signal analysis. Selection of electrodes is controlled by the microprocessor 194 via address/data bus 198, which selections may be varied as desired. Signals from the electrodes selected for coupling to bandpass amplifier 216 are provided to multiplexer 212, and thereafter converted to multi-bit digital signals by A/D converter 218, for storage in memory 196 under control of direct memory access circuit 220. Microprocessor 194 may employ digital signal analysis techniques to characterize the digitized signals stored in memory 196 to recognize and classify the patient's heart rhythm employing any of the numerous signal-processing methodologies known to the art. Microprocessor 194 may also employ digital signal analysis techniques to analyze the signal using known techniques to measure QT interval durations, and determine a need for increased cardiac output based on the QT interval durations. For example, microprocessor 194 may compare the measured QT intervals or the rate of change of the QT intervals to a threshold value stored in memory 196.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 194 into the timing/control circuitry 200, to control the operation of the escape interval counters therein and to define refractory periods during which detection of R-waves and P-waves is ineffective to restart the escape interval counters.

In the event that generation of a cardioversion or defibrillation pulse is required, microprocessor 194 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 194 activates cardioversion/defibrillation control circuitry 222, which initiates charging of the high voltage capacitors 166 and 168 via charging circuit 224, under the control of high voltage charging control line 226. The voltage on high voltage capacitors 166 and 168 is monitored via VCAP line 228, which is passed through multiplexer 212 and in response to reaching a predetermined value set by microprocessor 194, results in generation of a logic signal on Cap Full (CF) line 230 to terminate charging. Thereafter, timing/control circuit 200 controls timing of the delivery of the defibrillation or cardioversion pulse.

Delivery of cardioversion or defibrillation pulses is accomplished by output circuit 160 under the control of control circuitry 222 via control bus 198. Output circuit 160 determines whether a monophasic or biphasic pulse is delivered, the polarity of the electrodes and which electrodes are involved in delivery of the pulse. Output circuit 160 also includes high voltage switches, which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators.

Figure 5:
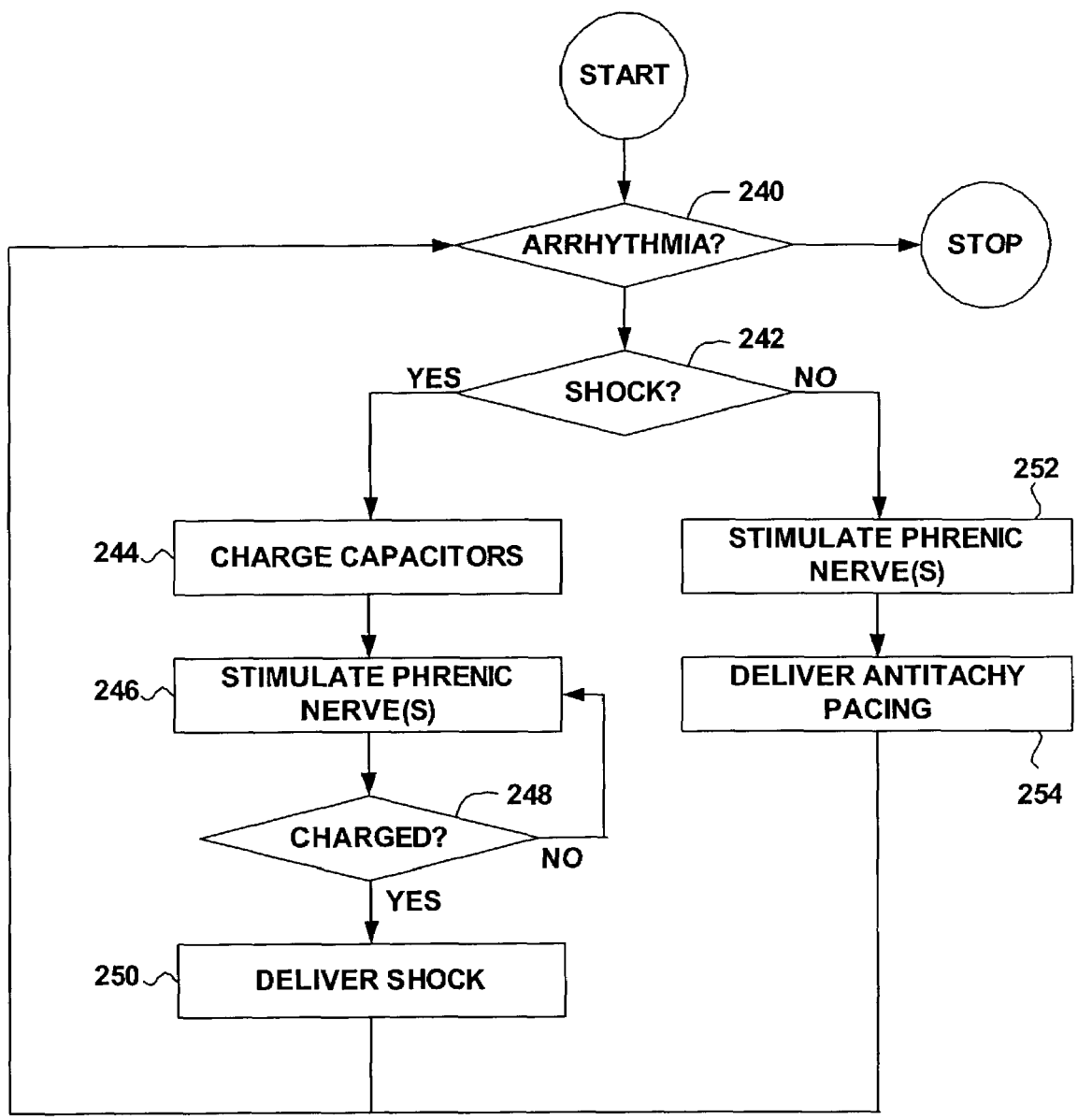
FIG. 5 is a flow diagram illustrating an exemplary method that may be employed by an implantable medical device to stimulate one or both phrenic nerves.

FIG. 5 is a flow diagram illustrating an exemplary method that may be employed by an IMD, such as IMD 150, to stimulate one or both of phrenic nerves 14. Microprocessor 194 detects a tachyarrhythmia (240). Microprocessor 194 may measure R-R intervals, P-P intervals, P R intervals and R-P intervals and detect tachyarrhythmias based on durations of these intervals.

Microprocessor 194 will determine whether the therapy it will provide to patient 12 in response to the detected tachyarrhythmia will be a shock, such as a defibrillation or cardioversion shock, or antitachyarrhythmia pacing (242). Microprocessor 194 may make this determination based on a classification of the rhythm. Microprocessor 194 may classify the rhythm using digital signal processing, as described above. Microprocessor 194 may also make this determination based on the next therapy within a pre-programmed progression of therapies.

If microprocessor 194 determines that it will deliver a shock to patient 12, microprocessor 194 may direct the charging of the high voltage capacitors 166 and 168 via charging circuit 224 (244), as described above. Microprocessor 194 may direct timing/control circuit 200 to direct one or more stimulation circuits 202-206 to stimulate one or both phrenic nerves 14 while capacitors 166 and 168 are charging (246). Timing/control circuit 200 may receive a signal indicating that the capacitors 166 and 168 are full (248), and direct delivery of the shock to patient 12 (250), at which time circuit 200 may suspend stimulation of phrenic nerves 14. If microprocessor 194 determines that it will deliver an antitachyarrhythmia pacing to patient 12, microprocessor 194 may direct timing/control circuit 200 to direct the stimulation of phrenic nerves 14 (252) during the delivery of antitachyarrhythmia pacing (254).

Figure 6:
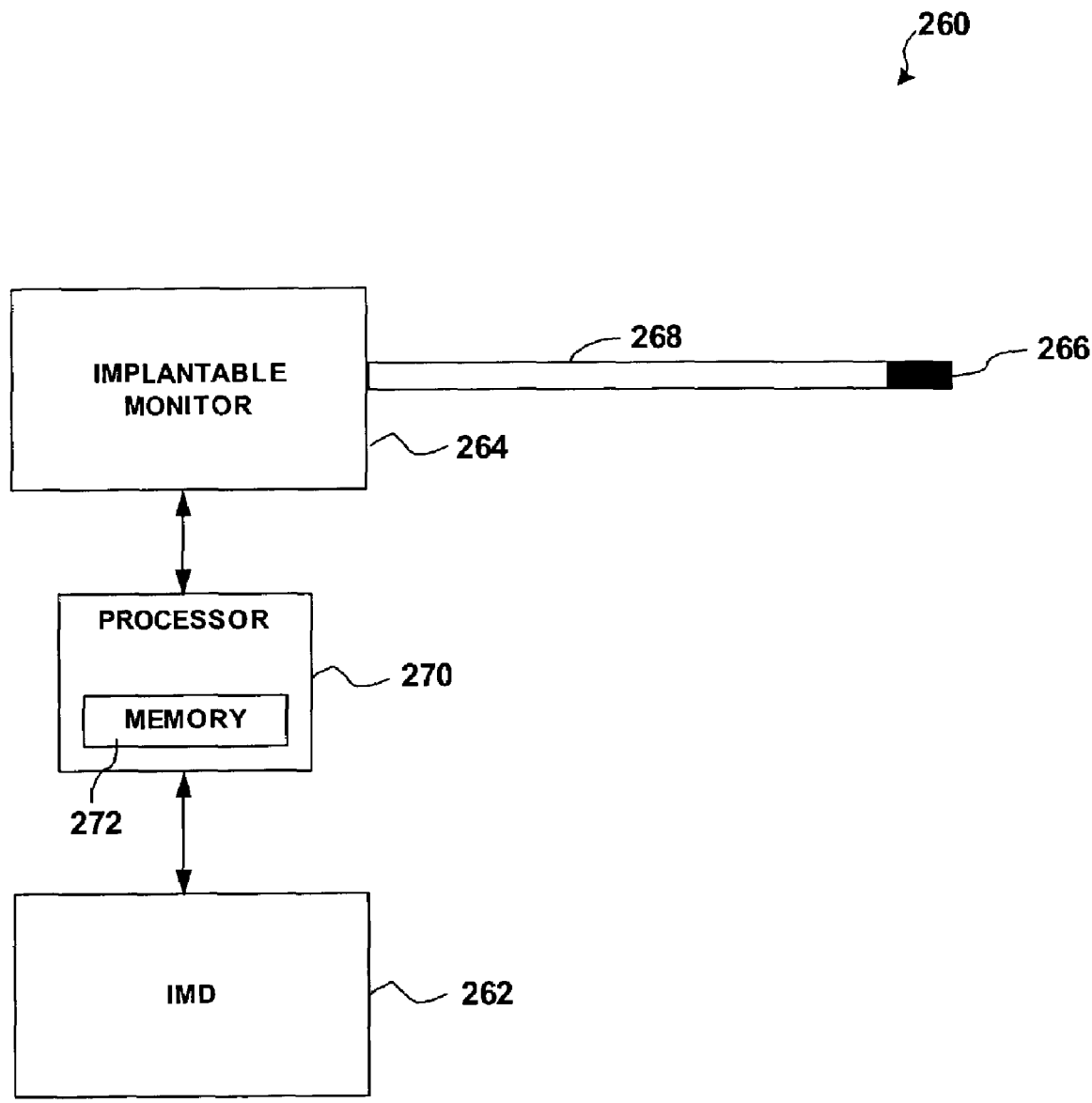
FIG. 6 is a block diagram of a system including an implantable medical device and a pressure monitor.

FIG. 6 is a block diagram of a system 260 illustrating an embodiment of the invention. As shown in FIG. 6, system 260, which may be implantable in a human being or a mammal, includes an IMD 262 and a implantable monitor 264 that monitors a physiological parameter that indicates a need for increased cardiac output, such as a pressure or blood oxygen saturation, via sensor 266 that is couple to monitor 264 by a lead 268. Monitor 262 may include any number of sensors 266 coupled to monitor 264 via one or more leads 268, however, for ease of illustration, a single sensor 266 coupled to monitor 264 via a single lead 268 is shown in FIG. 6.

IMD 262 receives a signal that indicates a need for increased cardiac output from monitor 264. IMD 262 may correspond to any of IMDs 10, 90 or 150 described above. IMD 262 stimulates one or both of phrenic nerves 14 via one or more of leads that include electrodes as described above. IMD 262 may also sense electrical activity within heart 20, deliver pacing pulses to heart 20, and/or deliver defibrillation shocks to heart 20 via leads and electrodes as described above.

In some embodiments, monitor 264 may be a pressure monitor that monitors a pressure within the cardiovascular system of patient 12 that indicates a need for increased cardiac output. Monitor 264 may receive pressure signals from sensor 266 via a lead 268. The pressure signals are a function of the absolute fluid pressure at the site where sensor 266 is disposed. In such embodiments, sensor 266 may be, for example, a capacitive or piezoelectric absolute pressure sensor, and may generate pressure signals itself or may modulate pressure signals conducted through lead 268. An example of pressure monitor 264 is the Chronicle™ Implantable Hemodynamic Monitor manufactured by and commercially available from Medtronic, Inc. of Minneapolis, Minn.

Sensor 266 may, for example, be located within right ventricle 26, and may monitor the pressure within right ventricle 26, and estimate the pulmonary artery diastolic pressure based on the rate of change over time of the pressure within right ventricle 26. Increased pulmonary artery diastolic pressure indicates inadequate cardiac output. The present invention is not limited to estimating the pulmonary artery diastolic pressure, or to pressure sensor locations in right ventricle. Monitor 264 may, for example, monitor arterial pulse pressure, central venous pressure, left ventricular end diastolic pressure, pulmonary capillary wedge pressure, or the like, from various pressure sensor locations within or outside of the circulatory system of patient 12.

In some embodiments, monitor 264 may be a blood oxygen saturation monitor that monitors one or both of the arterial and venous blood oxygen saturation of patient 12. Such embodiments of monitor 264 may also take the form of a Chronicle™ Implantable Hemodynamic Monitor, which in this case is modified to act as a blood oxygen saturation monitor. As mentioned above, decreased arterial or venous oxygen saturation, or an increased difference between the arterial and venous oxygen saturations indicates inadequate cardiac output. In such embodiments, sensor 266 is responsive to the oxygen saturation level of blood proximate to sensor 266. Sensor 266 may monitor blood oxygen saturation from any location within the circulatory system of patient.

Sensor 266 may include an emitter that emits light, e.g., infrared and red light, which is scattered and reflected by blood proximate to sensor 266. The emitter may include two light emitting diodes, one diode for red light (e.g., at a wavelength of approximately 660 nm), and one diode for infrared light (e.g., at a wavelength of approximately 880 nm). Red light reflects color variations that are proportional to the oxygen content in oxygenated hemoglobin. In addition, sensor 266 may include a receiver that receives light reflected from the blood proximate to sensor 266. In particular, the receiver may be sensitive to a particular wavelength of light. In an exemplary embodiment, the receiver may be an isolated, photo-sensitive diode that detects the reflected light and converts the magnitude to time intervals, which are inversely proportional to the oxygen content. Hence, the intensity of the received light is indicative of the oxygen saturation level in the blood. Reflected infrared light, independent of the oxyhemoglobin content, may be used as a reference. In particular, the interval between red and infrared light can be used as the expression of oxygen saturation. In this manner, the measurement can be made independently of variations in emission conditions affecting the reflected red and infrared light equally.

IMD 262 and monitor 264 are coupled to processor 270. Processor 270 is associated with memory 272. Processor 270 receives a pressure or blood oxygen saturation measured by monitor 264, determines whether the pressure or blood oxygen saturation indicates a need for increased cardiac output of heart 20, and delivers a signal to IMD 262 indicating the need based on the determination. Processor 270 may, for example, compare the received pressure or blood oxygen saturation level to a threshold value stored in memory 272, and, if the pressure exceeds the threshold value, deliver a signal to IMD 262. In other embodiments, processor 270 may instead compare the rate of increase in the pressure or rate of decrease of the blood oxygen saturation level to a threshold value. Processor 270 may execute software-implemented algorithms stored on memory 272.

Processor 270 is shown as logically separate from IMD 262 and monitor 264, but in practice processor 270 may be housed inside IMD 262 or monitor 264, or may be distributed among IMD 262 and monitor 264. Processor 270 may, for example, be included in microprocessors 104 of FIGS. 3 and 194 of FIG. 4, for example, in which case memory 272 may correspond to any of memories 102, 108 and 110 of FIG. 3, or memory 196 of FIG. 4. Moreover, IMD 262, monitor 264 and processor 270 may be realized as a single implantable device. In such embodiments, sensor 266 may be included on the same lead 16 as phrenic nerve 14 stimulating electrodes, as depicted in FIG. 2. The invention encompasses all of these variations.

Figure 7:
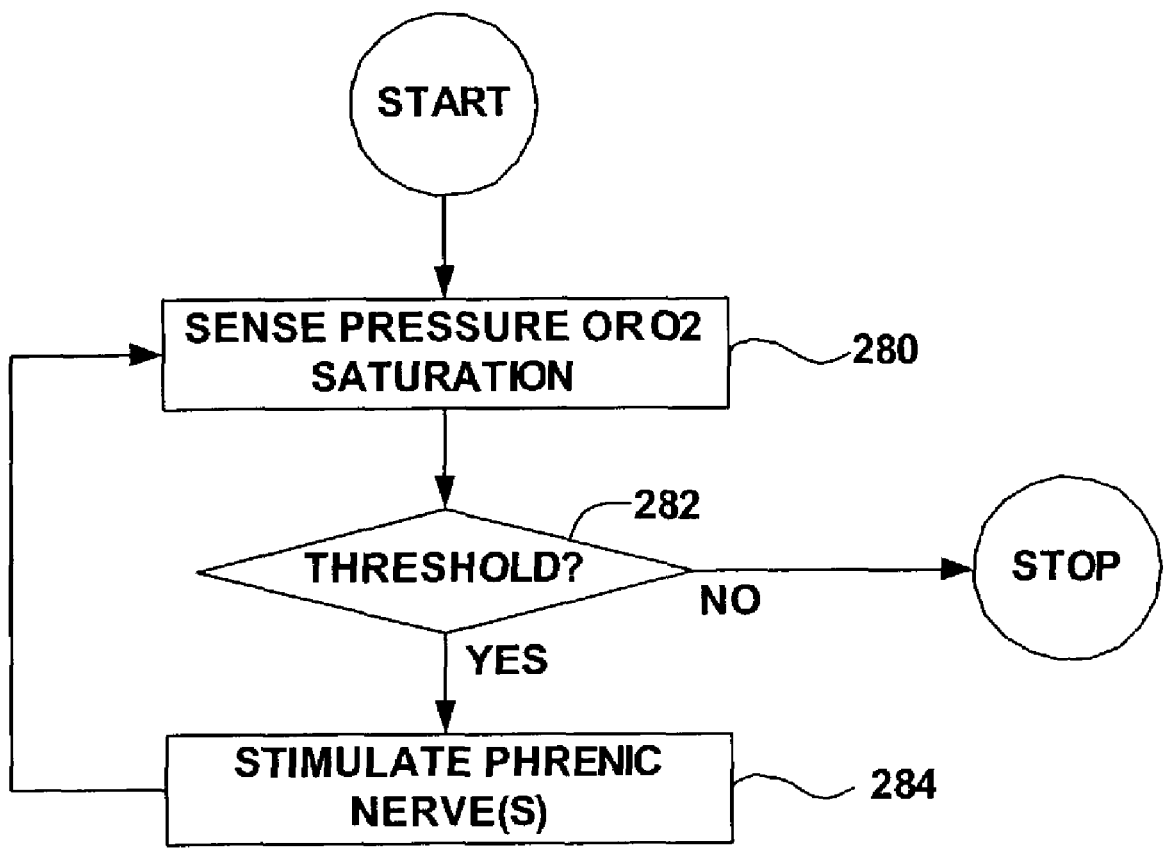
FIG. 7 is a flow diagram illustrating an exemplary method that may be employed by the system of FIG. 6 to stimulate one or both phrenic nerves.

FIG. 7 is a flow diagram illustrating an exemplary method that may be employed by the system 260 to stimulate one or both of phrenic nerves 14. Monitor 264 may sense a pressure or blood oxygen saturation within the circulatory system of patient 12 that indicates a need for increased cardiac output via sensor 266 (280). For example, monitor 264 may sense pressure within right ventricle 26 and estimate the pulmonary artery diastolic pressure. Processor 270 may receive the pressure or oxygen saturation measured by monitor 264, and compare it to a threshold value stored in memory 272 to determine if there is a need for increased cardiac output (282). Depending on the pressure or oxygen saturation measured or estimated by monitor 264, processor 270 may determine that there is a need for increased cardiac output of heart 20 if the pressure is above or below the threshold value. Processor 270 may also compare the rate of change of the pressure or oxygen saturation to a threshold value. If processor 270 determines that there is a need for increased cardiac output, processor 270 may deliver a signal to IMD 262 indicating the need, and IMD 262 may stimulate one or both phrenic nerves 14 in response to the signal (284). Processor 270 may continue to deliver the signal and IMD 262 may continue to stimulate the phrenic nerves so long as the sensed pressure indicates a need for increased cardiac output.

A number of embodiments and features of an IMD have been described. However, an IMD according the invention is not limited to these embodiments or features. For example, although IMDs have been described herein as stimulating phrenic nerves in order to increase cardiac output, other nerves associated with respiration may be stimulated instead of, or in addition to phrenic nerves. As one example, nerves associated with abdominal muscles and intercostals muscles, which play a role in respiration, particularly forceful expiration such as by a cough, and affect the volume of the thoracic cavity, may be stimulated by embodiments of an IMD consistent with the invention. Such embodiments of an IMD may include leads that carry electrodes to points proximate to the nerves associated with these expiratory muscles. Stimulation may, for example, be delivered to the lower thoracic/upper lumbar region of the spinal cord in order to stimulate these nerves.

Stimulation of expiratory nerves further reduces thoracic cavity volume to a volume less than the volume when the diaphragm is at rest, and may provide a greater increase in thoracic cavity pressure than that provided by recoil of the diaphragm as discussed above with reference to FIG. 1. In some embodiments, an IMD may first stimulate phrenic nerves and then shortly thereafter expiratory nerves, in a complimentary fashion, in order to achieve greater cyclical thoracic cavity pressure changes. These and other embodiments are within the scope of the following claims.

What is claimed is:

1. A method comprising:
receiving a signal that indicates a need for increased cardiac output of a heart of a patient;
stimulating a nerve associated with respiration of the patient in response to the signal, wherein stimulating a nerve further includes
detecting an intrinsic cardiac event;
stimulating the nerve based on the detection, wherein stimulating the nerve further comprises;
identifying a period of ventricular filling of the heart based on the detected event;
identifying a time to stimulate the nerve in order to decrease pressure within a thoracic cavity during the period of ventricular filling; and
stimulating the nerve at the identified time.

2. A method comprising:
receiving a signal that indicates a need for increased cardiac output of a heart of a patient;
stimulating a nerve associated with respiration of the patient in response to the signal, wherein stimulating a nerve further includes
detecting an intrinsic cardiac event;
stimulating the nerve based on the detection, wherein stimulating the nerve further comprises: identifying a period of ventricular contraction of the heart based on the detected event;
identifying a time to stimulate the nerve in order to increase pressure within a thoracic cavity during the period of ventricular contraction; and
stimulating the nerve at the identified time.

3. A device comprising:
an implantable medical device that receives a signal that indicates a need for increased cardiac output of a heart of a patient, and stimulates a nerve associated with respiration of the patient in response to the signal;
an electrode;
a processor to receive a signal that indicates a need for increased cardiac output of a heart of a patient, and direct an output circuit to stimulate a nerve associated with respiration of the patient via the electrode in response to the signal, wherein the processor detects an intrinsic cardiac event via the electrode, and directs the output circuit to stimulate the nerve based on the detection and the processor identifies a period of ventricular filling of the heart based on the detected event, identifies a time to stimulate the nerve in order to decrease pressure within a thoracic cavity during the period of ventricular filling, and stimulating the nerve at the identified time.

4. A device comprising:
an implantable medical device that receives a signal that indicates a need for increased cardiac output of a heart of a patient, and stimulates a nerve associated with respiration of the patient in response to the signal;
an electrode;
a processor to receive a signal that indicates a need for increased cardiac output of a heart of a patient, and direct an output circuit to stimulate a nerve associated with respiration of the patient via the electrode in response to the signal, wherein the processor detects an intrinsic cardiac event via the electrode, and directs the output circuit to stimulate the nerve based on the detection and the processor identifies a period of ventricular contraction of the heart based on the detected event, identifies a time to stimulate the nerve in order to increase pressure within a thoracic cavity during the period of ventricular contraction, and stimulating the nerve at the identified time.

5. The device of claim 4, wherein the electrode is a first electrode and the output circuit is a first output circuit, the device further comprising:
   a second electrode; and
   a second output circuit, wherein the processor directs the first output circuit to stimulate a right phrenic nerve via the first electrode, and directs the second output circuit to stimulate the left phrenic nerve via the second electrode.

6. A computer-readable medium comprising instructions that cause a processor to direct an output circuit to stimulate a nerve associated with respiration of a patient via an electrode in response to a signal that indicates a need for increased cardiac output of a heart of a patient and to detect an intrinsic cardiac event via the electrode, and wherein the instructions that cause a processor to direct the output circuit to stimulate the nerve comprise instructions that cause the processor to direct the output circuit to stimulate the nerve based on the detection, wherein the instructions that cause the processor to direct the output circuit to stimulate the nerve comprise instructions that cause a processor to:

identify a period of ventricular filling of the heart based on the detected event;
   identify a time to stimulate the nerve in order to decrease pressure within a thoracic cavity during the period of ventricular filling; and
   stimulate the nerve at the identified time.

7. A computer-readable medium comprising instructions that cause a processor to direct an output circuit to stimulate a nerve associated with respiration of a patient via an electrode in response to a signal that indicates a need for increased cardiac output of a heart of a patient and that cause a processor to detect an intrinsic cardiac event via the electrode, wherein the instructions that cause a processor to direct the output circuit to stimulate the nerve comprise instructions that cause the processor to direct the output circuit to stimulate the nerve based on the detection, wherein the instructions that cause a processor to direct the output circuit to stimulate the nerve comprise instructions that cause a processor to:

identify a period of ventricular contraction of the heart based on the detected event;
   identify a time to stimulate the nerve in order to increase pressure within a thoracic cavity during the period of ventricular contraction; and
   stimulate the nerve at the identified time.

* * * * *